(12) United States Patent
Chen et al.

(10) Patent No.: US 6,759,054 B2
(45) Date of Patent: Jul. 6, 2004

(54) ETHYLENE VINYL ALCOHOL COMPOSITION AND COATING

(75) Inventors: Yung-Ming Chen, Cupertino, CA (US); Ashok Shah, San Jose, CA (US); Vinayak D. Bhat, Sunnyvale, CA (US); Syed F. A. Hossainy, Fremont, CA (US); Daryush Mirzaee, Sunnyvale, CA (US); Evgenia Mandrusov, Campbell, CA (US); Deborra Sanders-Millare, San Jose, CA (US); Judy A. Guruwaiya, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 374 days.

(21) Appl. No.: 09/750,655

(22) Filed: Dec. 28, 2000

(65) Prior Publication Data

US 2001/0018469 A1 Aug. 30, 2001

Related U.S. Application Data

(63) Continuation-in-part of application No. 09/621,123, filed on Jul. 21, 2000, which is a continuation-in-part of application No. 09/540,242, filed on Mar. 31, 2000, and a continuation-in-part of application No. 09/470,559, filed on Dec. 23, 1999, which is a continuation-in-part of application No. 09/390,855, filed on Sep. 3, 1999, and a continuation-in-part of application No. 09/390,069, filed on Sep. 3, 1999.

(51) Int. Cl.$^7$ ................................................ A61K 9/00
(52) U.S. Cl. ..................... 424/423; 424/426; 428/213; 428/387; 514/772.3
(58) Field of Search ............................. 424/423, 426; 514/772.3; 428/213, 387

(56) References Cited

U.S. PATENT DOCUMENTS

| | | | |
|---|---|---|---|
| 2,072,303 A | 3/1937 | Herrmann et al. | 128/335.5 |
| 4,733,665 A | 3/1988 | Palmaz | 128/343 |
| 4,800,882 A | 1/1989 | Gianturco | 128/343 |
| 4,886,062 A | 12/1989 | Wiktor | 128/343 |
| 4,977,901 A | * 12/1990 | Ofstead | 600/585 |
| 4,985,285 A | * 1/1991 | Ichikawa et al. | 428/1.31 |
| 5,112,457 A | 5/1992 | Marchant | 204/165 |

(List continued on next page.)

FOREIGN PATENT DOCUMENTS

| | | |
|---|---|---|
| EP | O 301 856 | 2/1989 |
| EP | O 665 023 | 8/1995 |
| EP | 0 970 711 A2 | 1/2000 |
| WO | WO 91/12846 | 9/1991 |
| WO | WO 96/40174 | 12/1996 |
| WO | WO 97/45105 | 12/1997 |
| WO | WO 99/01118 | 1/1999 |
| WO | WO 99/63981 | 12/1999 |
| WO | WO 00/02599 | 1/2000 |
| WO | WO 00/12147 | 3/2000 |
| WO | WO 00/64506 | 11/2000 |
| WO | WO 01/01890 A1 | 1/2001 |

OTHER PUBLICATIONS

Miyazawa et al.; *Effects of Pemirolast and Tranilast on Intimal Thickening After Arterial Injury in the Rat*; J Cardiovasc Pharmacol 1997; 157–162.

Ohsawa et al.; *Preventive Effects of an Antiallergic Drug, Pemirolast Potassium, on Restenosis After Percutaneous Transluminal Coronary Angioplasty*; Am Heart J 1998; 136: 1081–7.

(List continued on next page.)

*Primary Examiner*—David W. Wu
*Assistant Examiner*—Henry S. Hu
(74) *Attorney, Agent, or Firm*—Squire, Sanders & Dempsey; Cameron K. Kerrigan

(57) ABSTRACT

An ethylene vinyl alcohol coating for an implantable device or prosthesis, such as a stent, is provided. Compositions are also provided for coating the implantable device. The compositions can include an ethylene vinyl alcohol copolymer added to an iso-propyl alcohol (IPA)/water solvent. Active agents, such as actinomycin D, can be included in the composition to be carried by the copolymer matrix.

15 Claims, 5 Drawing Sheets

U.S. PATENT DOCUMENTS

| | | | |
|---|---|---|---|
| 5,328,471 A | 7/1994 | Slepian | 604/101 |
| 5,455,040 A | 10/1995 | Marchant | 424/426 |
| 5,464,650 A | 11/1995 | Berg et al. | 427/2.3 |
| 5,578,073 A | 11/1996 | Haimovich et al. | 623/1 |
| 5,605,696 A | 2/1997 | Eury et al. | 424/423 |
| 5,628,730 A | 5/1997 | Shapland et al. | 604/21 |
| 5,667,767 A | 9/1997 | Greff et al. | 424/9.411 |
| 5,670,558 A | 9/1997 | Onishi et al. | 523/112 |
| 5,700,286 A | 12/1997 | Tartaglia et al. | 623/1 |
| 5,716,981 A | 2/1998 | Hunter et al. | 514/449 |
| 5,756,553 A * | 5/1998 | Iguchi et al. | 514/772.3 |
| 5,770,301 A * | 6/1998 | Murai et al. | 428/213 |
| 5,800,392 A | 9/1998 | Racchini | 604/96 |
| 5,824,049 A | 10/1998 | Ragheb et al. | 623/1 |
| 5,830,178 A | 11/1998 | Jones et al. | 604/49 |
| 5,837,313 A | 11/1998 | Ding et al. | 427/2.21 |
| 5,851,508 A | 12/1998 | Greff et al. | 424/9.411 |
| 5,858,746 A | 1/1999 | Hubbell et al. | 435/177 |
| 5,865,814 A | 2/1999 | Tuch | 604/265 |
| 5,873,904 A | 2/1999 | Ragheb et al. | 623/1 |
| 5,971,954 A | 10/1999 | Conway et al. | 604/96 |
| 5,980,928 A | 11/1999 | Terry | 424/427 |
| 5,980,972 A | 11/1999 | Ding | 427/2.24 |
| 6,010,530 A | 1/2000 | Goicoechea | 623/1 |
| 6,015,541 A | 1/2000 | Greff et al. | 424/1.25 |
| 6,042,875 A | 3/2000 | Ding et al. | 427/2.24 |
| 6,051,648 A | 4/2000 | Rhee et al. | 525/54.1 |
| 6,056,993 A | 5/2000 | Leidner et al. | 427/2.25 |
| 6,060,451 A | 5/2000 | DiMaio et al. | 514/13 |
| 6,080,488 A | 6/2000 | Hostettler et al. | 428/423.3 |
| 6,096,070 A | 8/2000 | Ragheb et al. | 623/1 |
| 6,099,562 A | 8/2000 | Ding et al. | 623/1.46 |
| 6,110,188 A | 8/2000 | Narciso, Jr. | 606/153 |
| 6,113,629 A | 9/2000 | Ken | 623/1.1 |
| 6,120,536 A | 9/2000 | Ding et al. | 623/1.43 |
| 6,120,904 A | 9/2000 | Hostettler et al. | 428/423.3 |
| 6,121,027 A | 9/2000 | Clapper et al. | 435/180 |
| 6,129,761 A | 10/2000 | Hubbell | 623/11 |
| 6,153,252 A | 11/2000 | Hossainy et al. | 427/2.3 |
| 6,165,212 A | 12/2000 | Dereume et al. | 623/1.13 |
| 6,258,121 B1 | 7/2001 | Yang et al. | 623/1.46 |
| 6,287,588 B1 * | 9/2001 | Shih et al. | 424/426 |
| 6,335,029 B1 * | 1/2002 | Kamath et al. | 424/423 |
| 6,368,658 B1 * | 4/2002 | Schwarz et al. | 427/2.15 |

OTHER PUBLICATIONS

Shozo Miyazaki, et al.; *Antitumor Effect of Implanted Ethylene–Vinyl Alcohol Copolymer Matrices Containing Anticancer Agents on Ehrlich Ascites Carcinoma and P388 Leukemia in Mice*; 1985; Chem. Pharm. Bull. vol. 33, No. 6, pp. 2490–2498.

Peter Barath, M.D. et al.; *Low Dose of Antitumor Agents Prevents Smooth Muscle Cell Proliferation After Endothelial Injury*; Feb. 1989; JACC vol. 13, No. 2, p. 252 A.

Taku Shigeno; *Prevention of Cerebrovascular Spasm by Bosentan, Novel Endothelin Receptor*; 1996; Kanto Rosai Hosp., Kawasaki, 211, Japan; 6(4), 416–421.

Yuji Matsumaru et al.; *Embolic Materials For Endovascular Treatment Of Cerebral Lesions*; 1997; J. Biomater. Sci. Polymer Edn. vol. 8, No. 7, pp. 555–569.

* cited by examiner

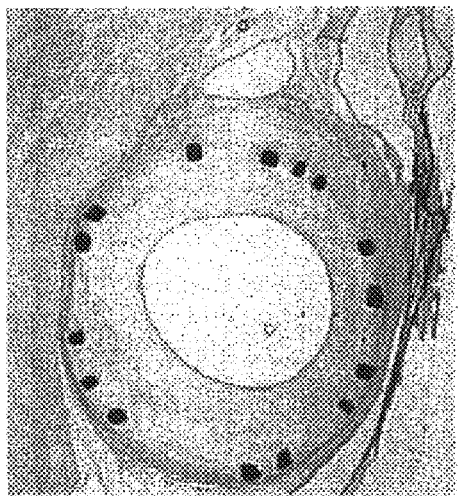
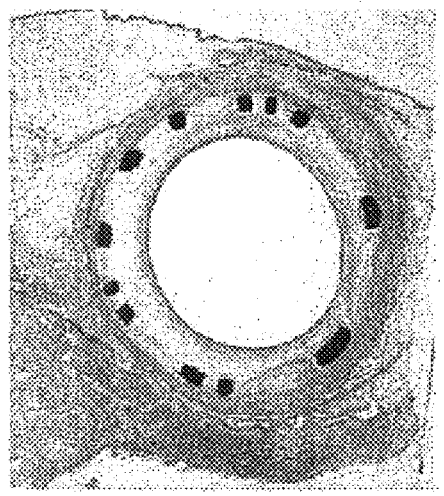
FIG. 5A                    FIG. 5B
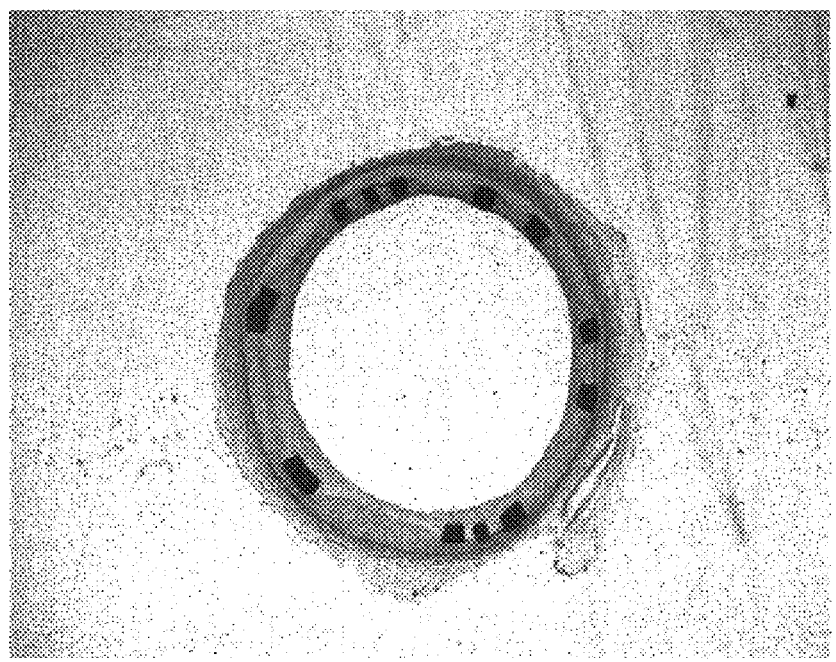
FIG. 6A

ETHYLENE VINYL ALCOHOL COMPOSITION AND COATING

CROSS-REFERENCE

This is a continuation-in-part of U.S. patent application Ser. No. 09/470,559 filed on Dec. 23, 1999 which is a continuation-in-part of U.S. patent application Ser. No. 09/390,855, filed Sep. 3, 1999 and Ser. No. 09/390,069, filed Sep. 3, 1999; and is a continuation-in-part of U.S. patent application Ser. No. 09/621,123 filed on Jul. 21, 2000, which is a continuation-in-part of U.S. patent application Ser. No. 09/540,242 filed on Mar. 31, 2000.

BACKGROUND OF THE INVENTION

1. Field of the Invention

This invention relates to a coating for an implantable device or an endoluminal prosthesis, such as a stent. The invention also relates to a biocompatible carrier containing an active agent for sustained release of the active agent to certain target cell population in a vascular region, such as smooth muscle cells, requiring modulation to ameliorate a diseased state, particularly for the treatment of stenosis or restenosis following a vascular trauma or disease. More specifically, the invention is directed to an ethylene vinyl alcohol composition and coating.

2. Description of the Background

Percutaneous transluminal coronary angioplasty (PTCA) is a procedure for treating heart disease. A catheter assembly having a balloon portion is introduced percutaneously into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to radially press against the atherosclerotic plaque of the lesion for remodeling of the vessel wall. The balloon is then deflated to a smaller profile to allow the catheter to be withdrawn from the patient's vasculature.

A problem associated with the above procedure includes formation of intimal flaps or torn arterial linings which can collapse and occlude the conduit after the balloon is deflated. Moreover, thrombosis and restenosis of the artery may develop over several months after the procedure, which may require another angioplasty procedure or a surgical by-pass operation. To reduce the partial or total occlusion of the artery by the collapse of arterial lining and to reduce the chance of the development of thrombosis and restenosis, an expandable, intraluminal prosthesis, one example of which includes a stent, is implanted in the lumen to maintain the vascular patency.

Stents are used not only as a mechanical intervention but also as a vehicle for providing biological therapy. As a mechanical intervention, stents act as scaffoldings, functioning to physically hold open and, if desired, to expand the wall of the passageway. Typically stents are capable of being compressed, so that they can be inserted through small cavities via catheters, and then expanded to a larger diameter once they are at the desired location. Examples in patent literature disclosing stents which have been successfully applied in PTCA procedures include stents illustrated in U.S. Pat. No. 4,733,665 issued to Palmaz, U.S. Pat. No. 4,800,882 issued to Gianturco, and U.S. Pat. No. 4,886,062 issued to Wiktor. Mechanical intervention via stents, although a significant innovation in the treatment of occlusive regions, has not reduced the development of restenosis.

Biological therapy can be achieved by medicating the stents. Medicated stents provide for the local administration of a therapeutic substance at the diseased site. In order to provide an efficacious concentration to the treated site, systemic administration of such medication often produces adverse or toxic side effects for the patient. Local delivery is a preferred method of treatment in that smaller total levels of medication are administered in comparison to systemic dosages, but are concentrated at a specific site. Local delivery thus produces fewer side effects and achieves more favorable results.

One proposed method for medicating stents disclosed seeding the stents with endothelial cells (Dichek, D. A. et al. Seeding of Intravascular Stents With Genetically Engineered Endothelial Cells; Circulation 1989; 80: 1347–1353). Briefly, endothelial cells were seeded onto stainless steel stents and grown until the stents were covered. The cells were therefore able to be delivered to the vascular wall where they provided therapeutic proteins. Another proposed method of providing a therapeutic substance to the vascular wall included use of a heparin-coated metallic stent, whereby a heparin coating was ionically or covalently bonded to the stent. Significant disadvantages associated with the aforementioned methods include significant loss of the therapeutic substance from the body of the stent during delivery and expansion of the stent, lack of control of the release rate of the proteins from the stent, and the inherent limitation as to the type of therapeutic substance that can be used.

Another proposed method involved the use of a polymeric carrier coated onto the surface of a stent, as disclosed in U.S. Pat. No. 5,464,650 issued to Berg et al. Berg disclosed applying to a stent body a solution which included a specified solvent, a specified polymer dissolved in the solvent, and a therapeutic substance dispersed in the blend. The solvent was allowed to evaporate, leaving on the stent surface a coating of the polymer and the therapeutic substance impregnated in the polymer. Among the specified, suitable choices of polymers listed by Berg, empirical results were specifically provided for poly(caprolactone) and poly (L-lactic acid). The preferred choice of mutually compatible solvents included acetone or chloroform. As indicated by Berg, stents where immersed in the solution 12 to 15 times or sprayed 20 times. The evaporation of the solvent provided a white coating. A white coloration is generally indicative of a brittle polymeric coating. A brittle polymeric coating is an undesirable characteristic, since portions of the coating typically become detached during stent expansion. Detachment of the coating causes the quantity of the therapeutic substance to fall below a threshold level sufficient for the effective treatment of a patient.

Accordingly, it is desirable to provide an improved coating that is susceptible to expanding with a prosthesis without significant detachment from the surface of the prosthesis. It is also desirable for the coating to be able to strongly adhere to the surface of the prosthesis, thereby preventing significant loss of the polymeric coating during prosthesis delivery. It is also desirable to provide a benign or friendly solvent system that is capable of placing the polymeric material in dissolution without causing or propagating significant degradation of the therapeutic substance. Other desirable features include, but are not limited to, a polymeric coating which allows for a significant control of the release rate of a therapeutic substance, a polymeric solution which need not be applied excessively to the surface of the prosthesis to form a coating of a suitable thickness, and a polymeric solution that allows for the deposition of a more uniform coating.

SUMMARY OF THE INVENTION

In accordance with one aspect of the present invention, a coating for a prosthesis, such as a balloon-expandable stent, a self-expandable stent, or a graft, is provided. The coating includes an ethylene vinyl alcohol copolymer that has an ethylene content which makes the copolymer capable of dissolving in a solvent comprising iso-propyl alcohol and water. The copolymer can comprise a mole percent of ethylene of about 27% to about 29%. On commercial example of the copolymer is Soarnol®.

In one embodiment, the copolymer can include an active agent such as actinomycin D, paclitaxel, or docetaxel. The active agent can be for inhibiting abnormal or inappropriate migration or proliferation of smooth muscle cells. In another embodiment, the copolymer can act as an intermediary tie layer between a metallic surface of the prosthesis and a coating layer carrying an active agent. In yet another embodiment, the copolymer can act as a diffusion barrier disposed over a coating layer carrying an active agent for reducing the rate at which the active agent is released from the coating layer.

In accordance with another aspect of the present invention, a therapeutic composition for inhibiting the narrowing of a region of a blood vessel is provided. The composition includes an ethylene vinyl alcohol copolymer and an active agent. The copolymer comprises a mole percent of ethylene monomer of about 27% to about 29%. The active agent can be released from the copolymer matrix to inhibit the narrowing of a region of the blood vessel. The narrowing can be caused by, for example, restenosis. Examples of agents include, actinomycin D, paclitaxel, or decetaxel.

In accordance with another aspect of the present invention, a method is provided for forming a coating for a prosthesis, such as a stent. The method comprises applying a composition including an ethylene vinyl alcohol copolymer and a solvent to the prosthesis to form a coating. The copolymer can include a mole percent of ethylene of about 27% to about 29%. The solvent includes iso-propyl alcohol and water such that the coating is formed by allowing the solvent to evaporate. In accordance with one embodiment, the composition that is applied to the prosthesis is heated to a temperature greater than about the glass transition temperature and less than about the melting temperature of the copolymer.

In accordance with one embodiment, the composition can additionally include an active agent for inhibiting restenosis or the narrowing of the blood vessel such that the active agent is releasably contained in the coating formed on the prosthesis. Examples of such agents include actinomycin D, paclitaxel, docetaxel, or analogs or derivatives thereof.

BRIEF DESCRIPTION OF THE FIGURE

FIG. 5A is a picture of a histology slide of a coronary vessel from the control group in accordance with Example 3;

FIG. 5B is a picture of a histology slide of a coronary vessel from the actinomycin D group in accordance with Example 3;

FIG. 6A is a picture of a histology slide of a coronary vessel from the control group in accordance with Example 4.

DETAILED DESCRIPTION OF THE EMBODIMENTS

Embodiments of the Composition

The embodiments of the composition are prepared by conventional methods wherein all components are combined, then blended. More particularly, in accordance to one embodiment, a predetermined amount of an ethylene vinyl alcohol copolymer (commonly known by the generic name EVOH or by the trade name EVAL) is added to a predetermined amount of iso-propyl alcohol (IPA) admixed with water, i.e., IPA/$H_2O$ solvent. If necessary, heating, stirring and/or mixing can be employed to effect dissolution of the copolymer into the IPA/$H_2O$ solvent, for example 4 hours in a water bath at about 80° C.

Figure 1A:
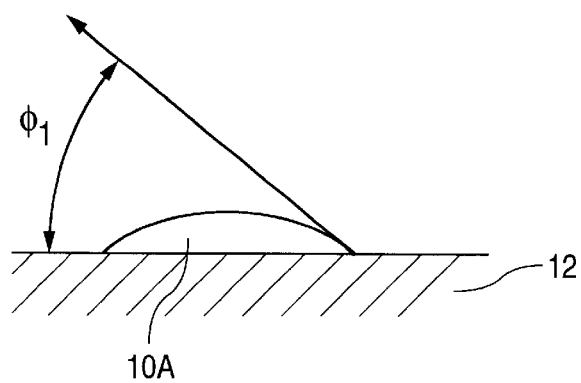
FIG. 1A illustrates a fluid on a solid substrate having a contact angle $\Phi_1$.
Figure 1B:
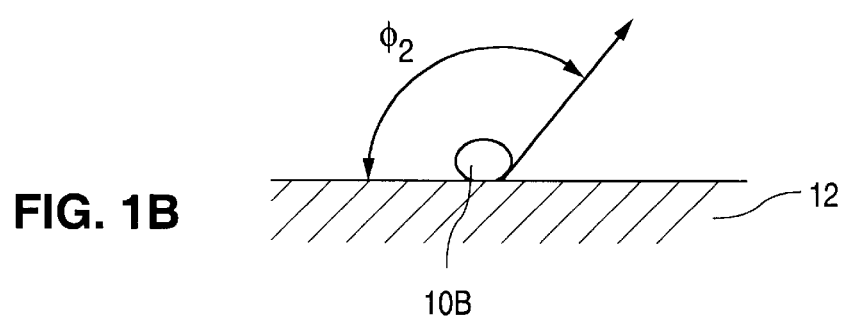
FIG. 1B illustrates a fluid on a solid substrate having a contact angle $\Phi_2$.

IPA can comprise from about 40% to about 60%, more narrowly about 45% to about 55%, typically about 50% by weight of the of the total weight of the IPA/$H_2O$ solvent. IPA/$H_2O$ solvent is not only capable of placing the low ethylene content (e.g., 29 mol %) copolymer into dissolution, but allows for lower processing temperatures for the formation of the coating onto the device. Processing temperatures of, for example, ambient temperature to about 50° C. can be employed. Lower processing temperatures are advantageous in that most therapeutic or active agents, such as actinomycin D, react adversely to heat, more particularly when combined with a solvent system. The IPA/$H_2O$ solvent also provides a stable platform for most therapeutic substances. The solvent serves as a more compatible or benign solution as it does not adversely react with or propagate the degradation of most therapeutic or active agents. Additionally, the IPA/$H_2O$ solvent enhances the wetting of the composition for a more uniform application of the copolymer onto the surface of the device. "Wetting" is defined by capillary permeation. Capillary permeation is the movement of a fluid on a solid substrate driven by interfacial energetics. Capillary permeation is quantitated by a contact angle, defined as an angle at the tangent of a droplet in a fluid phase that has taken an equilibrium shape on a solid surface. A low contact angle means a higher wetting liquid. A suitably high capillary permeation corresponds to a contact angle less than about 90°. FIG. 1A illustrates a fluid droplet 10A on a solid substrate 12, for example a stainless steel surface. Fluid droplet 10A has a high capillary permeation that corresponds to a contact angle $\Phi_1$, which is less than about 90°. In contrast, FIG. 1B illustrates a fluid droplet 10B on solid substrate 12, having a low capillary permeation that corresponds to a contact angle $\Phi_2$, which is greater than about 90°.

Ethylene vinyl alcohol copolymer refers to copolymers comprising residues of both ethylene and vinyl alcohol monomers. One of ordinary skill in the art understands that an ethylene vinyl alcohol copolymer may also be a terpolymer so as to include small amounts of additional monomers, for example less than about five (5) mole percentage of styrenes, propylene, or other suitable monomers. The copolymer should comprise a mole percent of ethylene equal to or less than what is necessary to achieve dissolution of the copolymer in the IPA/H$_2$O solvent. About 27% to about 29% mole percent ethylene content is capable of dissolving in the IPA/H$_2$O solvent.

One commercial example of an ethylene vinyl alcohol copolymer having 29% mole percentage is known by the registered mark of Soarnol®, more particularly Soarnol® D2908 (available from: (1) US and NAFTA Markets: Soarus L.L.C., 3930 Ventura Drive, Suite 440, Arlington Heights, Ill. 60004, U.S.A.; (2) Asian Markets: The Nippon Synthetic Chemical Industry Co., Ltd, Umeda Sky Building, 1–88, Oyodonaka 1-chome, Kita-ku, Osaka, Japan (Postal Code) 531–6029; and (3) European Markets: Nippon Gohsei Europe GmbH Prinzenallel13, D-40549 Duesseldorf Germany). General properties of Soarnol® D2908 are listed in Table 1:

TABLE 1

| Properties | Unit | Value |
|---|---|---|
| Ethylene Content | mol % | 29 |
| Melt Index[1] | g/10 min | 8 |
| (at 210° C., 21.168(N) {2160 g} | | |
| Melting Point[2] | ° C. | 188 |
| Crystallization Temp. | ° C. | 163 |
| Glass Transition Temp. | ° C. | 62 |

[1]Melt Indexcer
[2]DSC, both heating and cooling speeds of 20° C./min

By way of example, the ethylene vinyl alcohol copolymer can comprise from about 0.1% to about 35%, more narrowly from about 1% to about 10% by weight of the total weight of the composition; and the IPA/H$_2$O solvent can comprise from about 65% to about 99.9%, more narrowly from about 90% to about 99% by weight of the total weight of the composition. A specific weight ratio is dependent on factors such as the material from which the prosthesis is made, the geometrical structure of the prosthesis, and the coating application technique employed.

Active Agent

In accordance with another embodiment, sufficient amounts of an active agent or therapeutic substance for causing preventative or therapeutic effects can be dispersed in the blended composition of the ethylene vinyl alcohol copolymer and the IPA/H$_2$O solvent. As a general rule, an increase in the amount of the ethylene comonomer content decreases the rate that the active agent is released from the copolymer matrix. The release rate of the active agent typically decreases as the hydrophilicity of the copolymer decreases. An increase in the amount of the ethylene comonomer content increases the overall hydrophobicity of the copolymer, especially as the content of vinyl alcohol is concomitantly reduced.

In this embodiment, by way of example, the ethylene vinyl alcohol copolymer can comprise from about 0.1 to about 35%, more narrowly from about 1% to about 10% by weight of the total weight of the composition; the IPA/H$_2$O solvent can comprise from about 59.9% to about 99.8%, more narrowly from about 85% to about 98.9 by weight of the total weight of the composition; and the active agent can comprise from about 0.1% to about 40%, more narrowly from about 0.1% to about 5% by weight of the total weight of the composition. Selection of a specific weight ratio of the ethylene vinyl alcohol copolymer and the IPA/H$_2$O solvent is dependent on factors such as the material from which the device is made, the geometrical structure of the device, the type and amount of the active agent employed, and the coating application technique employed.

In accordance with another embodiment, of a second solvent can be used to improve the solubility of the active agent in the composition. Accordingly, higher active agent concentrations can be formulated. Sufficient amounts of a second solvent, for example, methanol, tetrahydrofuran (THF), dimethylformamide (DMF), dimethyl acetamide (DMAC), and mixtures and combinations thereof, can be added to the blended composition. Alternatively, the active agent can be added to the second solvent prior to admixture with the composition.

The particular weight percentage of the active agent mixed within the composition, with or without the second solvent, depends on factors such as duration of the release, cumulative amount of release, and release rate that is desired. It is known that the release rate and the cumulative amount of the active agent that is released is directly proportional to the total initial content of the agent in the copolymer matrix. Accordingly, a wide spectrum of release rates can be achieved by modifying the ethylene comonomer content and the initial amount of the active agent.

The active agent should be in true solution or saturated in the blended composition. If the active agent is not completely soluble in the composition, operations including mixing, stirring, and/or agitation can be employed to effect homogeneity of the residues. The active agent may be added so that dispersion is in fine particles. The mixing of the active agent can be conducted at ambient pressure, and at room temperature such that supersaturating the active ingredient is not desired.

The active agent should inhibit the activity of vascular smooth muscle cells. More specifically, the active agent is aimed at inhibiting abnormal or inappropriate migration and proliferation of smooth muscle cells.

"Smooth muscle cells" include those cells derived from the medial and adventitia layers of the vessel which proliferate in intimal hyperplastic vascular sites following vascular trauma or injury. Under light microscopic examination, characteristics of smooth muscle cells include a histological morphology of a spindle shape with an oblong nucleus located centrally in the cell with nucleoli present and myofibrils in the sarcoplasm. Under electron microscopic examination, smooth muscle cells have long slender mitochondria in the juxtanuclear sarcoplasm, a few tubular elements of granular endoplasmic reticulum, and numerous clusters of free ribosomes. A small Golgi complex may also be located near one pole of the nucleus.

"Migration" of smooth muscle cells means movement of these cells in vivo from the medial layers of a vessel into the intima, such as may also be studied in vitro by following the motion of a cell from one location to another, e.g., using time-lapse cinematography or a video recorder and manual counting of smooth muscle cell migration out of a defined area in the tissue culture over time.

"Proliferation" of smooth muscle cells means increase in cell number.

"Abnormal" or "inappropriate" proliferation means division, growth or migration of cells occurring more rapidly or to a significantly greater extent than typically occurs in a normally functioning cell of the same type, i.e., hyperproliferation.

"Inhibiting" cellular activity means reducing, delaying or eliminating smooth muscle cell hyperplasia, restenosis, and vascular occlusions, particularly following biologically or mechanically mediated vascular injury or trauma or under conditions that would predispose a mammal to suffer such a vascular injury or trauma. As used herein, the term "reducing" means decreasing the intimal thickening that results from stimulation of smooth muscle cell proliferation. "Delaying" means retarding the progression of the hyperproliferative vascular disease or delaying the time until onset of visible intimal hyperplasia, as observed, for example, by histological or angiographic examination. "Elimination" of restenosis following vascular trauma or injury means completely "reducing" and/or completely "delaying" intimal hyperplasia in a patient to an extent which makes it no longer necessary to surgically intervene, i.e., to re-establish a suitable blood flow through the vessel by, for example, repeat angioplasty, atheroectomy, or coronary artery bypass surgery. The effects of reducing, delaying, or eliminating restenosis may be determined by methods known to one of ordinary skill in the art, including, but not limited to, angiography, ultrasonic evaluation, fluoroscopy imaging, fiber optic visualization, or biopsy and histology. Biologically mediated vascular injury includes, but is not limited to injury caused by or attributed to autoimmune disorders, alloimmune related disorders, infectious disorders including endotoxins and herpes viruses such as cytomegalovirus, metabolic disorders such as atherosclerosis, and vascular injury resulting from hypothermia and irradiation. Mechanical mediated vascular injury includes, but is not limited to vascular injury caused by catheterization procedures or vascular scraping procedures such as percutaneous transluminal coronary angioplasty, vascular surgery, stent placement, transplantation surgery, laser treatment, and other invasive procedures which disrupted the integrity of the vascular intima or endothelium. The active ingredient of the invention is not restricted in use for therapy following vascular injury or trauma; rather, the usefulness of the active ingredient will also be determined by the ingredient's ability to inhibit cellular activity of smooth muscle cells or inhibit the development of restenosis.

In one embodiment, the active agent is actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. Actinomycin D is represented by the molecular formula $C_{62}H_{86}N_{12}O_{16}$, and is generally depicted by the following structure:

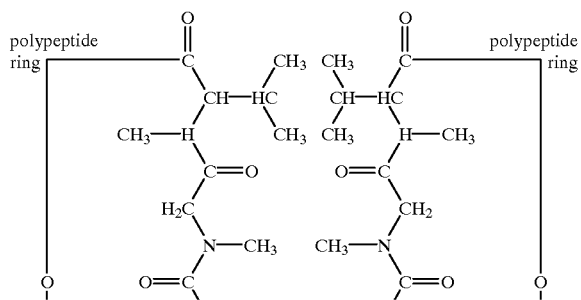

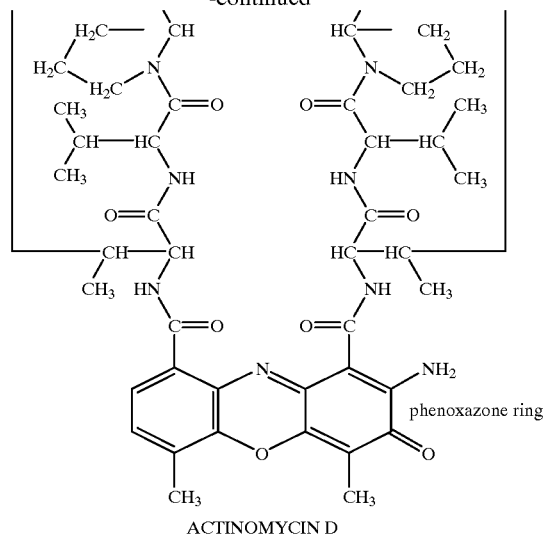

ACTINOMYCIN D

The active agent can also include any substance capable of exerting a therapeutic or prophylactic effect in the practice of the present invention. The agent can also be for enhancing wound healing in a vascular site and improving the structural and elastic properties of the vascular site. Examples of agents include other antiproliferative substances as well as antineoplastic, antiinflammatory, antiplatelet, anticoagulant, antifibrin, antithrombin, antimitotic, antibiotic, antioxidant, and combinations thereof. Examples of suitable antineoplastics include paclitaxel and docetaxel. Examples of suitable antiplatelets, anticoagulants, antifibrins, and antithrombins include sodium heparin, low molecular weight heparin, hirudin, argatroban, forskolin, vapiprost, prostacyclin and prostacyclin analogs, dextran, D-phe-pro-arg-chloromethylketone (synthetic antithrombin), dipyridamole, glycoprotein IIb/IIIa platelet membrane receptor antagonist, recombinant hirudin, thrombin inhibitor (available from Biogen), and 7E-3B® (an antiplatelet drug from Centocore). Examples of suitable antimitotic agents include methotrexate, azathioprine, vincristine, vinblastine, fluorouracil, adriamycin, and mutamycin. Examples of suitable cytostatic or antiproliferative agents include angiopeptin (a somatostatin analog from Ibsen), angiotensin converting enzyme inhibitors such as CAPTOPRIL (available from Squibb), CILAZAPRIL (available from Hoffinan-LaRoche), or LISINOPRIL (available from Merck); calcium channel blockers (such as Nifedipine), colchicine, fibroblast growth factor (FGF) antagonists, fish oil (omega 3-fatty acid), histamine antagonist, LOVASTATIN (an inhibitor of HMG-CoA reductase, a cholesterol lowering drug from Merck), monoclonal antibodies (such as PDGF receptors), nitroprusside, phosphodiesterase inhibitors, prostaglandin inhibitor (available form Glazo), Seramin (a PDGF antagonist), serotonin blockers, steroids, thioprotease inhibitors, triazolopyrimidine (a PDGF antagonist), and nitric oxide. Other therapeutic substances or agents which may be appropriate include alpha-interferon, genetically engineered epithelial cells, and dexamethasone.

The dosage or concentration of the active agent required to produce a favorable therapeutic effect should be less than the level at which the active agent produces toxic effects and greater than the level at which non-therapeutic results are obtained. The dosage or concentration of the active agent required to inhibit the desired cellular activity of the vascular region can depend upon factors such as the particular circumstances of the patient; the nature of the trauma; the nature of the therapy desired; the time over which the ingredient administered resides at the vascular site; and if other therapeutic agents are employed, the nature and type of the substance or combination of substances. Therapeutic effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

Implantable Devices or Prostheses

The device used in conjunction with the above-described composition may be any suitable prosthesis, examples of which include self-expandable stents, balloon-expandable stents, and grafts. The underlying structure of the device can be virtually any design. The device can be made of a metallic material or an alloy such as, but not limited to, cobalt chromium alloy (ELGILOY), stainless steel (316L), "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable or biostable polymers could also be used with the blended composition. A polymeric implantable device should be compatible with the composition. The ethylene vinyl alcohol copolymer, however, adheres very well to metallic materials, more specifically to stainless steel.

Methods for Coating

To form a coating on a surface of the implantable device or prosthesis, the surface of the device should be clean and free from contaminants that may be introduced during manufacturing. However, the surface of the device requires no particular surface treatment to retain the applied coating. The composition can be applied to both the inner and outer (the tissue contacting) surfaces of the device. Application of the composition can be by any conventional method, such as by spraying the composition onto the device or immersing the device in the composition. Operation such as wiping, centrifugation, atomizing, or other web clearing acts can be performed to achieve a more uniform coating. Briefly, wiping refers to the physical removal of excess coating from the surface of the device, e.g., stent; centrifugation refers to rapid rotation of the stent about an axis of rotation; atomizing refers to atomization of the coating solution into small droplets and deposits over the surface of the device. The excess coating can also be vacuumed or blown off the surface of the device.

To form an optional primer layer on the surface of the device, an embodiment of the composition free from any active agents is applied to the surface of the device. Subsequent to the application of the composition, the composition should be exposed to a heat treatment at a temperature range of greater than about the glass transition temperature and less than about the melting temperature of the copolymer (for example a temperature range of about 120° C. to 160° C). The device should be exposed to the heat treatment for any suitable duration of time (e.g., 30 minutes) which would allow for the formation of the primer coating on the surface of the device and allows for the evaporation of the solvent. The primer can be used for increasing the retention of a reservoir coating containing an active agent on the surface of the device, particularly metallic surfaces such as stainless steel. The primer can act as an intermediary adhesive tie region between the surface of the device and the coating carrying the active ingredient—which, in effect, allows for the quantity of the active agent to be increased in the reservoir region of the coating.

For the formation of the coating containing an active agent, an embodiment of the composition containing an active agent is applied to the device. If a primer layer is employed, the application should be performed subsequent to the drying of the primer. The IPA/$H_2O$ solvent or the combination of the IPA/$H_2O$ solvent and second solvent is removed from the composition applied to the surfaces of the device by allowing the IPA/$H_2O$ solvent or combination of the IPA/$H_2O$ solvent and the second solvent to evaporate. Heating the device at a predetermined temperature for a predetermined period of time can induce evaporation.

An optional diffusion barrier can be formed over the reservoir coating containing the active agents. An embodiment of the composition, free from any active agents, can be applied to a selected portion of the reservoir region subsequent to the drying of the reservoir region. The solvent is then allowed to evaporate by, for example, exposure to a selected temperature, to form the diffusion barrier. For the diffusion barriers, higher ethylene content copolymers, such as 44 mol %, can be used to further reduce the rate of release of the active agent. For higher ethylene content copolymers, a dimethylsulfoxide (DMSO) solvent can be used to effect dissolution.

For the reservoir coating containing the active agent and the optional diffusion barrier, the heat treatment should be, for example, conducted at about 30° C. to about 50° C. for about 15 minutes to no longer than 4 hours. Higher degrees of temperature may adversely affect the characteristics of the active agent. The heating can be conducted in an anhydrous atmosphere and at ambient pressure. The heating can, alternatively, be conducted under a vacuum condition. It is understood that essentially all of the solvent(s) will be removed from the composition but traces or residues can remain blended with the copolymer.

Coating

Figure 2A:
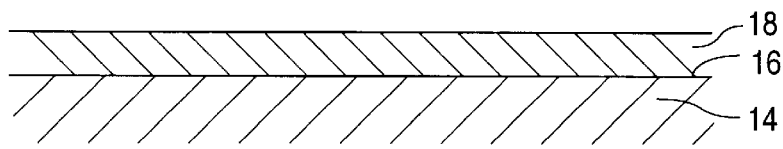
FIGS. 2A–2D illustrate coatings in accordance to some of the embodiments of the present invention.

FIGS. 2A–2D illustrate some of the various embodiments for the coating layers in accordance with the present invention. FIGS. 2A–2D have not been drawn to scale and the thickness of the layers have been over or under emphasized for illustrative purposes. FIG. 2A illustrates a surface 16 of a stent 14 having an ethylene vinyl alcohol reservoir coating 18. Reservoir coating 18 contains an active agent such as actinomycin D. The ethylene vinyl alcohol copolymer is a biocompatible coating, i.e., a coating which, in the amounts employed, is non-toxic, non-inflammatory, chemically inert, and substantially non-immunogenetic. The copolymer also includes a high percentage of —OH functional group which is susceptible to attachment of active agents as well as further surface modification-such as specific interaction with a secondary —OH functional group. The inclusion of the active agent in the copolymer matrix allows for not only the retention of the active ingredient on stent 14 during delivery and, if applicable, expansion of stent 14, but also the controlled and sustained administration of the active agent following implantation. By way of example, and not limitation, the impregnated ethylene vinyl alcohol copolymer reservoir coating 18 can have a thickness of about 0.5 microns to about 5 microns. The particular thickness of reservoir coating 18 is based on the type of procedure for which prosthesis is employed and the amount of the active ingredient that is desired to be delivered. Applying a plurality of reservoir coating layers onto the prosthesis can further increase the amount of the active ingredient to be included on the prosthesis. The application of each layer should be performed subsequent to the evaporation of the solvent(s) and the drying of the copolymer of the previous layer.

Figure 2B:
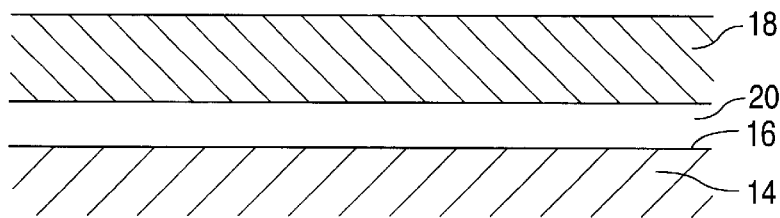

Referring to FIG. 2B, there is illustrated stent 14 carrying reservoir coating 18. An intermediary primer layer 20 can be deposited on surface 16. Primer layer 20 can be made from an ethylene vinyl alcohol copolymer, free from any active agents. The use of ethylene vinyl alcohol copolymer as the optional primer layer 20 serves as a functionally suitable intermediary layer between surface 16 and reservoir coating 18. Ethylene vinyl alcohol copolymer adheres well to metallic surfaces, particularly stainless steel. Accordingly, the copolymer, free from any active agents, provides for a good adhesive tie between reservoir coating 18 and surface 16. By way of example and not limitation, primer layer 20 can have a thickness of about 0.1 microns to about 2 microns.

Figure 2C:
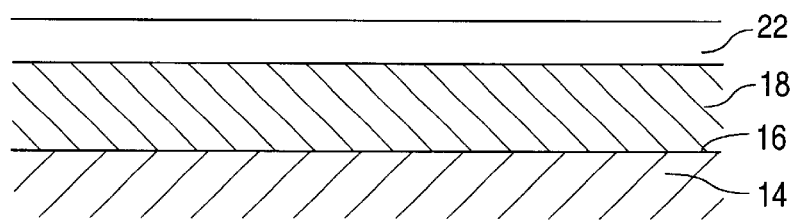

In another embodiment, as illustrated in FIG. 2C, a diffusion barrier coating 22 is disposed on reservoir coating 18. Diffusion barrier coating 22 can be made from an ethylene vinyl alcohol copolymer. By way of example, and not limitation, the diffusion barrier 22 can have a thickness of about 0.25 microns to about 4.0 microns. It is understood by one of ordinary skill in the art that the thickness of the diffusion barrier 22 is based on factors such as the type stent 14, type of procedure for which stent 14 is employed and the rate of release that is desired.

Figure 2D:
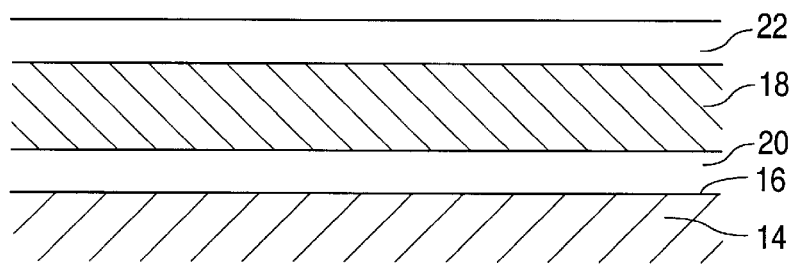

In accordance with another embodiment, referring to FIG. 2D, stent 14 includes primer 20, reservoir coating 18 and diffusion barrier coating 22. One of ordinary skill in the art will understand that a variety of other configurations and layering patterns can be employed with the present invention. The deposition of each layer should be performed subsequent to the evaporation of the solvent(s) and the drying of the polymer of the previous layer.

Method of Use

In accordance with the above-described method, the active agent can be applied to an implantable device or prosthesis, e.g., a stent, retained on the stent during delivery and expansion of the stent, and released at a desired control rate and for a predetermined duration of time at the site of implantation. The release rate of the active agent can be controlled by modifying release parameters such as the amount of ethylene comonomer content of the copolymer and the initial active ingredient content in the matrices of the copolymer. The rate of release can also be adjusted by the addition of a diffusion barrier layer. A stent having the above-described coating is useful for a variety of medical procedures, including, by way of example, treatment of obstructions caused by tumors in bile ducts, esophagus, trachea/bronchi and other biological passageways. A stent having the above-described coating is particularly useful for treating occluded regions of blood vessels caused abnormal or inappropriate migration and proliferation of smooth muscle cells, thrombosis, and restenosis. Stents may be placed in a wide array of blood vessels, both arteries and veins. Representative examples of sites include the iliac, renal, and coronary arteries.

Briefly, an angiogram is first performed to determine the appropriate positioning for stent therapy. Angiogram is typically accomplished by injecting a radiopaque contrasting agent through a catheter inserted into an artery or vein as an x-ray is taken. A guidewire is then advanced through the lesion or proposed site of treatment. Over the guidewire is passed a delivery catheter which allows a stent in its collapsed configuration to be inserted into the passageway. The delivery catheter is inserted either percutaneously or by surgery into the femoral artery, brachial artery, femoral vein, or brachial vein, and advanced into the appropriate blood vessel by steering the catheter through the vascular system under fluoroscopic guidance. A stent having the above described coating may then be expanded at the desired area of treatment. A post insertion angiogram may also be utilized to confirm appropriate positioning.

EXAMPLES

The embodiments of the invention will be illustrated by the following set forth examples which are being given by way of illustration only and not by way of limitation. All parameters and data are not be construed to unduly limit the scope of the embodiments of the invention.

Example 1

Figure 3:
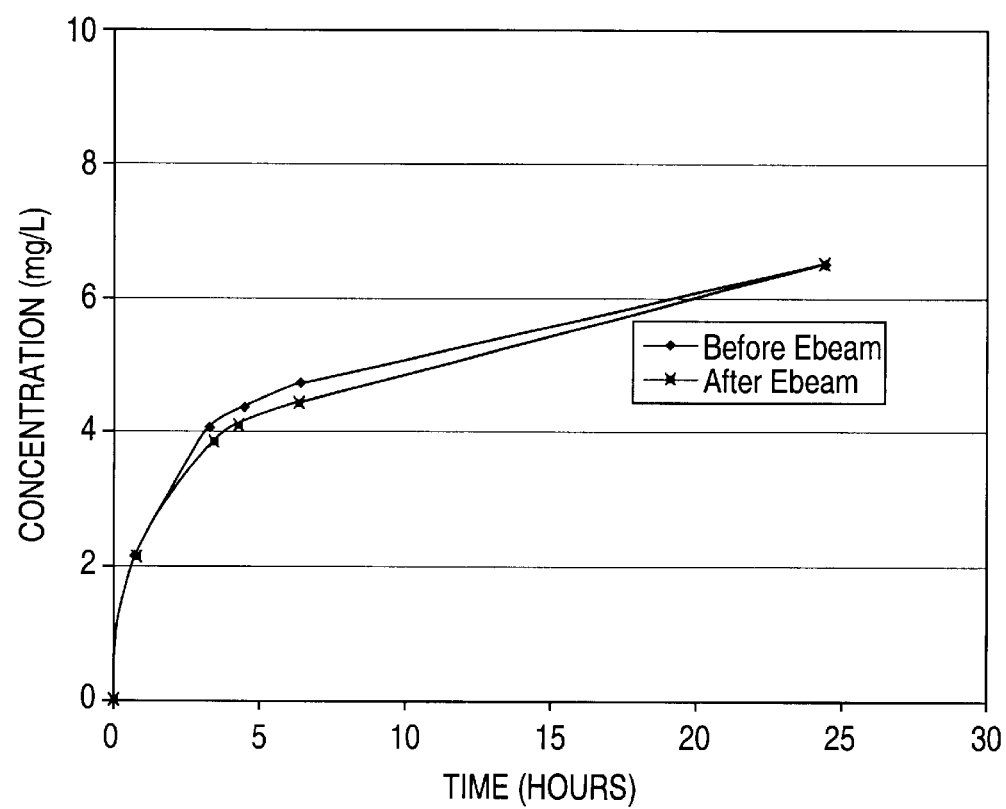
FIG. 3 graphically illustrates elution profiles for stents with a coating of ethylene vinyl alcohol copolymer impregnated with vinblastine made according to Example 1.

Multi-Link™ stents were cleaned by placement in an ultrasonic bath of isopropyl alcohol solution for 10 minutes. The stents were dried and plasma cleaned in a plasma chamber. An EVOH (44 mol %) solution was made with 1 gram of EVOH and 7 grams of DMSO, making an EVOH:DMSO ratio of 1:7. Vinblastine was added to the 1:7 EVOH:DMSO solution. Vinblastine constituted 2.5% by weight of the total weight of the solution. The solution was vortexed and placed in a tube. The cleaned Multi-Link™ stents were attached to mandrel wires and dipped into the solution. The coated stents were passed over a hot plate, for about 3–5 seconds, with a temperature setting of about 60° C. The coated stents were cured for 6 hours in an air box then placed in a vacuum oven at 60° C. for 24 hours. The above process was repeated twice, having a total of three layers. The average weight of the coating was 0.00005 gram, with an estimated vinblastine concentration of 12 microgram per stent. Some of the stents were sterilized by electron beam radiation. The sterilized and unsterilized vinblastine coated stents were tested for a 24 hour elution period by placing one sterilized and one unsterilized stent in 5 ml of phosphated saline solution (pH 7.4) at room temperature with rotational motion. The amount of vinblastine eluted was evaluated by High Performance Liquid Chromatography (HPLC) analysis. The results of this test are given below and plotted in FIG. 3. The data indicates that electron beam radiation procedure does not interfere in the release of vinblastine from EVOH.

| Release Profile For Vinblastine - Unsterilized | | | |
|---|---|---|---|
| Time (Hours) | microgram Released | Total microgram Released | microgram Release per Hour |
| 0 | 0 | 0 | 0 |
| 0.5 | 2.12 | 2.12 | 4.24 |
| 3 | 1.91 | 4.03 | 0.76 |
| 4 | 0.27 | 4.30 | 0.27 |
| 6 | 0.38 | 4.68 | 0.19 |
| 24 | 1.7 | 6.38 | 0.09 |

| Release Profile For Vinblastine - Sterilized | | | |
|---|---|---|---|
| Time (Hours) | ug Release | Total uG Released | uG Release per Hour |
| 0 | 0 | 0 | 0 |
| 0.5 | 2.14 | 2.14 | 4.28 |
| 3 | 1.7 | 3.84 | 0.68 |
| 4 | 0.28 | 4.12 | 0.28 |
| 6 | 0.26 | 4.38 | 0.13 |
| 24 | 2.05 | 6.43 | 0.11 |

Example 2

Inhibition of SMC Proliferation with Actinomycin D

Figure 4:
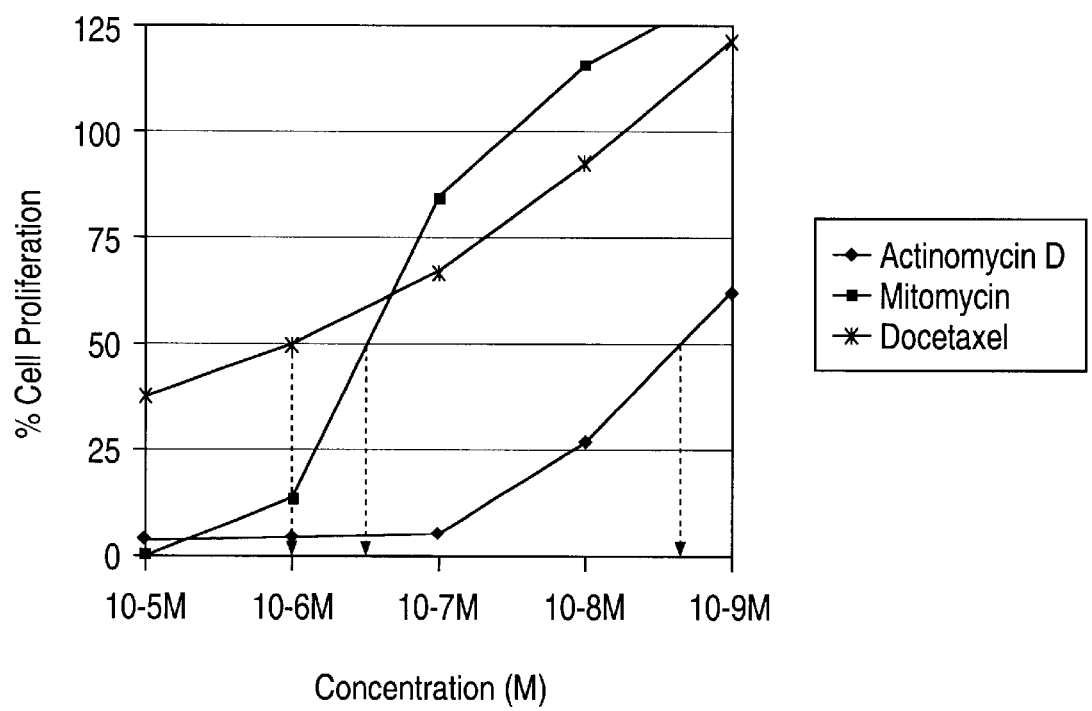
FIG. 4 graphically illustrates in vitro experimental data, in accordance with Example 2, showing affects of actinomycin D, mitomycin, and docetaxel on smooth muscle cell proliferation.

Medial smooth muscle cells (SMC) were isolated from rat aorta and cultured according to explant methods known to one of ordinary skill in the art. Cells were harvested via trypsinization and subcultivated. Cells were identified as vascular SMC through their characteristic hill-and-valley growth pattern as well as indirect immunofluorescence with monoclonal anti SMC α-actin. Studies were performed with cells at passage 3–4. SMC monlayers were established on 24 well culture dishes, scrape wounded and treated with actinomycin D, mytomycin and docetaxel. The cells were exposed to the drug solution of different concentrations for 2 hours and then washed with buffered saline solution. The proliferation of the cells was quantified by standard technique of thymidine incorporation. The results from the study are tabulated in FIG. 4.

The $IC_{50}$ (concentration at which 50% of the cells stop proliferating) of actinomycin D was $10^{-9}M$ as compared to $5 \times 10^{-5}M$ for mitomycin and $10^{-6}M$ for docetaxel. Actinomycin D was the most potent agent to prevent SMC proliferation as compared to other pharmaceutical agents.

Example 3

Reduction in Restenosis in the Porcine Coronary Artery Model

Porcine coronary models were used to assess the degree of the inhibition of neointimal formation in the coronary arteries of a porcine stent injury model by Actinomycin D, delivered with a microporous balloon catheter ($1 \times 10^6$ pores/$mm^2$ with sizes ranging from 0.2–0.8 micron).

The preclinical animal testing was performed in accordance with the NIH Guide for Care and Use of Laboratory Animals. Domestic swine were utilized to evaluate effect of the drug on the inhibition of the neointimal formation. Each testing procedure, excluding the angiographic analysis at the follow-up endpoints, was conducted using sterile techniques. During the study procedure, the activated clotting time (ACT) was monitored regularly to ensure appropriate anticoagulation. Base line blood samples were collected for each animal before initiation of the procedure. Quantitative coronary angiographic analysis (QCA) and intravascular ultrasound (IVUS) analysis was used for vessel size assessment.

The vessels at the sites of the delivery were denuded by inflation of the PTCA balloons to 1:1 balloon to artery ratio and moving the balloons back and forth 5 times. The drug was delivered to the denuded sites at 3.5 atm (3.61 Kg/sq cm) for 2 minutes using the microporous balloon catheters before stent deployment. The average volume of delivery was about 3.3+/−1.2 ml. Following drug delivery, stents were deployed at the delivery site such that final stent to artery ratio was 1.1:1.

QCA and IVUS analyses were used for stent deployment guidance. Pre-stenting IVUS measurements of the lumen size at the targeted vessel sites were performed for determination of the balloon (size) inflation pressure. Quantitative analysis of the stented coronary arteries to compare pre-stenting, post-stenting, follow-up minimal luminal diameters, stent recoil, and balloon/stent to artery ratio were performed. Following stent implantation and final angiogram, all devices were withdrawn and the wounds closed; the animals were allowed to recover from anesthesia as managed by the attending veterinarian or animal care professionals at the research center.

Upon return to the research laboratory at the 28-day endpoint, angiographic assessments were performed. Coronary artery blood flow was assessed and the stented vessels were evaluated to determine minimal lumen diameter. The animals were euthanized following this procedure at the endpoint. Following euthanasia, the hearts were pressure perfusion fixed with formalin and prepared for histological analysis, encompassing light microscopy, and morphometry. Morphometric analysis of the stented arteries included assessment of the position of the stent struts and determination of vessel/lumen areas, percent (%) stenosis, injury scores, intimal and medial areas and intima/media ratios. Percent stenosis is quantitated by the following equation:

$$100 \, (IEL \text{ area} - \text{lumen area})/IEL \text{ area}$$

where IEL is the internal elastic lamia.

The control group of animals received delivery of water instead of the drug. The test group of animals received actinomycin D in two different concentration of $10^{-5}M$ and $10^{-4}M$. The results of the study are tabulated in Table 1. The percent stenosis in the treated groups (32.3+/−11.7) was significantly decreased as compared to the control groups (48.8+/−9.8). FIGS. 5A and 5B illustrate sample pictures of the histology slides of the coronary vessels from the control and the Dose 1 group, respectively.

TABLE 1

|  | CONTROL 0M | DOSE 1 1E-05M | DOSE 2 1E-04M | t test (significant if p < 0.05) | |
|---|---|---|---|---|---|
|  | (n = 9) | (n = 10) | (n = 7) | p~ | p* |
| ANGIOGRAPHIC DATA (QCA) | | | | | |
| Percent Diameter Stenosis | 48.8 +/− 9.8 | 36.8 +/− 9.7 | 32.3 +/− 11.7 | 0.02 | 0.01 |
|  | CONTROL 0M | DOSE 1 1E-05M | DOSE 2 1E-04M | t test (significant if p < 0.05) | |
|  | (n = 27) | (n = 30) | (n = 21) | p~ | p* |
| HISTOMORPHOMETRIC DATA | | | | | |
| Percent Stenosis (IEL area-lumen area)/IEL area | 63.4 +/− 12.7 | 51.8 +/− 13.8 | 54.1 +/− 11.7 | 0.002 | 0.01 |

TABLE 1-continued

| | | | | | |
|---|---|---|---|---|---|
| Residual Lumen (Lumen area)/IEL area | 0.36 +/− 0.16 | 0.49 +/− 0.14 | 0.46 +/− 0.08 | 0.002 | 0.01 |

~comparison between control and Dose 1
*comparison between control and Dose 2

The results of the in vitro and in vivo standard test procedures demonstrate that actinomycin D is useful for the treatment of hyper-proliferative vascular disease. Specifically, actinomycin D is useful for the inhibition of smooth muscle cell hyperplasia, restenosis and vascular occlusion in a mammal, particularly occlusions following a mechanically mediated vascular trauma or injury.

Example 4

Positive Remodeling of the Vessel Wall Using Actinomycin D

In vivo data is provided illustrated positive remodeling caused by the application of actinomycin D. Stents coated with EVAL impregnated with actinomycin D and a control group of stents coated with EVAL free from actinomycin D were implanted in porcine coronary arteries. The animals were sacrificed at the end of 28 days. The EEL area of the actinomycin D-loaded vessels was statistically significantly greater than the EEL area of the control vessels. The index of remodeling was 1.076 (8.54/7.94).

IEL

| Condition | Mean Area | Std Dev |
|---|---|---|
| Drug coated(Act-D in EVAL) | 7.47 | 0.89 |
| Control (EVAL) | 6.6 | 0.61 |
| p value | 0.0002 | Statistical significant difference |

EEL (external elastic lamia)

| Condition | Mean Area | Std Dev |
|---|---|---|
| Drug coated(Act-D in EVAL) | 8.54 | 0.87 |
| Control (EVAL) | 7.94 | 0.73 |
| p value | 0.014 | Statistical significant difference |

EEL Area (mm2)

| ID # | Control | ID # | Actinomycin D | ID # | EVAL |
|---|---|---|---|---|---|
| 48 LCX d | 6.3966 | 63 LCX d | 7.4498 | 63 LAD d | 8.3037 |
| 48 LCX m | 7.4601 | 63 LCX m | 8.2509 | 63 LAD m | 8.8545 |
| 48 LCX p | 7.3063 | 63 LCX p | 7.7342 | 63 LAD p | 9.4698 |
| 49 LAD d | 8.5573 | 63 RCA d | 7.9207 | 64 LCX d | 7.8063 |
| 49 LAD m | 8.5187 | 63 RCA m | 6.9926 | 64 LCX m | 7.1117 |
| 49 LAD p | 6.6346 | 63 RCA p | 8.3883 | 64 LCX p | 7.2411 |
| 58 LAD d | 8.6078 | 65 LAD d | 7.8546 | 64 RCA d | 8.3383 |
| 58 LAD m | 8.1674 | 65 LAD m | 9.2545 | 64 RCA m | 8.0793 |
| 58 LAD p | 8.3775 | 65 LAD p | 9.2515 | 64 RCA p | 8.3652 |

EEL Area (mm2)

| ID # | Control | ID # | Actinomycin D | ID # | EVAL |
|---|---|---|---|---|---|
| 59 LCA d | 8.3054 | 68 LAD d | 8.7854 | 65 LCX d | 6.4638 |
| 59 LCX m | 7.3713 | 68 LAD m | 9.5164 | 65 LCX m | 7.1493 |
| 59 LCX p | 7.8662 | 68 LAD p | 9.1504 | 65 RCA d | 8.5955 |
| 59 RCA d | 7.3714 | 69 LCX d | 9.6679 | 65 RCA m | 8.0855 |
| 59 RCA m | 6.6783 | 69 LCX m | 9.1237 | 65 RCA p | 8.4785 |
| 59 RCA p | 7.4707 | 69 LCX p | 9.9849 | 68 LCX d | 8.4723 |
| 62 LCX d | 7.8784 | 69 RCA d | 9.4765 | 68 LCX m | 7.8382 |
| 62 LCX m | 7.5318 | 69 RCA m | 7.4424 | 68 LCX p | 8.0570 |
| 62 LCX p | 6.2647 | 69 RCA p | 9.1462 | 68 RCA d | 8.4840 |
| 62 RCA d | 8.3240 | 70 LCX d | 8.9504 | 68 RCA p | 8.8767 |
| 62 RCA m | 7.9535 | 70 LCX m | 8.9117 | 69 LAD d | 6.6648 |
| 62 RCA p | 8.5454 | 70 LCX p | 8.7533 | 69 LAD m | 6.8614 |
| 67 LAD d | 8.9532 | 70 RCA d | 7.3249 | 69 LAD p | 7.7632 |
| 67 LAD m | 9.2410 | 70 RCA m | 7.1061 | 70 LAD d | 7.5175 |
| 67 LAD p | 8.3841 | 70 RCA p | 8.5830 | 70 LAD m | 7.8630 |
| | | | | 70 LAD p | 8.2222 |
| AVG | 7.8402 | | 8.5425 | | 7.9475 |
| SD | 0.8046 | | 0.8755 | | 0.7349 |

Actin vs EVAL

| | |
|---|---|
| p = | 0.014709 |
| AVG % EEL growth | 7.486304 |

IEL Area (mm²)

| ID # | Control | ID # | Actinomycin D | ID # | EVAL |
|---|---|---|---|---|---|
| 48 LCX d | 5.2178 | 63 LCX d | 6.3785 | 63 LAD d | 6.9687 |
| 48 LCX m | 6.2108 | 63 LCX m | 7.5206 | 63 LAD m | 7.3908 |
| 48 LCX p | 6.1125 | 63 LCX p | 6.9992 | 63 LAD p | 7.3563 |
| 49 LAD d | 7.2848 | 63 RCA d | 6.9632 | 64 LCX d | 6.4420 |
| 49 LAD m | 7.4117 | 63 RCA m | 6.0418 | 64 LCX m | 6.0064 |
| 49 LAD p | 5.9918 | 63 RCA p | 7.4794 | 64 LCX p | 5.9970 |
| 58 LAD d | 7.2049 | 65 LAD d | 6.2324 | 64 RCA d | 6.8001 |
| 58 LAD m | 6.9334 | 65 LAD m | 8.3785 | 64 RCA m | 6.8561 |
| 58 LAD p | 6.9454 | 65 LAD p | 8.5819 | 64 RCA p | 7.0172 |
| 59 LCA d | 7.2640 | 68 LAD d | 8.0964 | 65 LCX d | 5.2485 |
| 59 LCX m | 6.2014 | 68 LAD m | 8.6879 | 65 LCX m | 6.1135 |
| 59 LCX p | 6.7283 | 68 LAD p | 8.0914 | 65 RCA d | 7.1525 |
| 59 RCA d | 6.0519 | 69 LCX d | 8.7181 | 65 RCA m | 6.4815 |
| 59 RCA m | 5.9992 | 69 LCX m | 8.0273 | 65 RCA p | 7.1775 |
| 59 RCA p | 5.9032 | 69 LCX p | 8.5222 | 68 LCX d | 6.9571 |
| 62 LCX d | 6.5329 | 69 RCA d | 8.3796 | 68 LCX m | 6.5724 |
| 62 LCX m | 6.2804 | 69 RCA m | 6.4219 | 68 LCX p | 6.7740 |
| 62 LCX p | 4.9303 | 69 RCA p | 7.7757 | 68 RCA d | 7.2425 |
| 62 RCA d | 7.0977 | 70 LCX d | 7.5392 | 68 RCA p | 7.5554 |
| 62 RCA m | 6.7466 | 70 LCX m | 7.6573 | 69 LAD d | 5.5505 |
| 62 RCA p | 7.1747 | 70 LCX p | 6.9749 | 69 LAD m | 5.5571 |
| 67 LAD d | 8.0264 | 70 RCA d | 6.2815 | 69 LAD p | 6.2697 |

-continued

IEL Area (mm²)

| ID # | Control | ID # | Actinomycin D | ID # | EVAL |
|---|---|---|---|---|---|
| 67 LAD m | 8.1144 | 70 RCA m | 5.9760 | 70 LAD d | 6.3212 |
| 67 LAD p | 7.2091 | 70 RCA p | 7.6195 | 70 LAD m | 6.6518 |
|  |  |  |  | 70 LAD p | 6.9032 |
| AVG | 6.6489 |  | 7.4727 |  | 6.6025 |
| SD | 0.7883 |  | 0.8972 |  | 0.6130 |

| Actin vs EVAL | |
|---|---|
| p = | 0.000283 |
| AVG % IEL growth | 13.17981 |

Figure 6B:
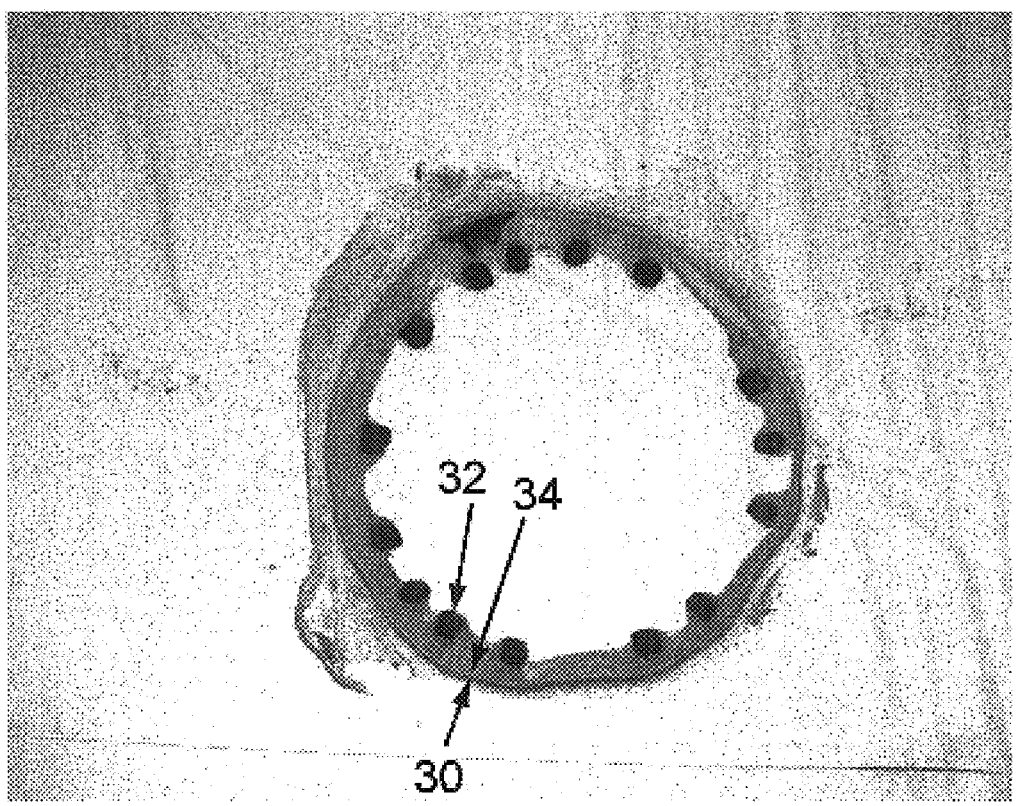
FIG. 6B is a picture of a histology slide of a coronary vessel from the actinomycin D group in accordance with Example 4.

FIGS. 6A and 6B illustrate sample pictures of the histology slides of the coronary vessels from the control group 64 RCA (Right Coronary Group) and the actinomycin loaded stent group 68 LAD (Left Anterior Descending), respectively. The stent used was an Advanced Cardiovascular Systems Multi-Link Duet™ (stainless steel). As is illustrated by FIG. 6B, the positive remodeling of IEL 30, caused by the application of actinomycin D, creates a gap between stent struts 32 and IEL 30. Thrombus deposites, illustrated by reference number 34, are formed in the gap over time. The use of a self-expandable stent can eliminate the formation of the gap as the stent self-expands in response to the positive remodeling of IEL. Thrombus deposits are, accordingly, eliminated.

Actinomycin D induces the positive remodeling of the vessel walls, more particularly positive remodeling of the external elastic lamina (EEL) of a blood vessel wall. Positive remodeling is generally defined as the ability of the vessel walls to structurally adapt, by increasing in lumen size, to chronic stimuli. A positively remodeled lumen wall has a greater diameter or size as compared to a lumen wall which has not been subjected to the remodeling effect. Accordingly, the flow of blood through the remodeled site is increased—flow which would have otherwise been reduced because of, for example, the presence of plaque build-up or migration and proliferation of cells. The index of remodeling is defined by the ratio of the area circumscribed by the EEL of the lesion site to the area circumscribed by the EEL of a reference site. As a result of the positive remodeling of the EEL, the internal elastic lamina (IEL), in response, can also increases in area or diameter. Actinomycin D, or analogs or derivative thereof, not only can inhibit abnormal or inappropriate migration and/or proliferation of smooth muscle cells, which can lead to restenosis, but can also induce positive remodeling of the blood vessel walls. Thus the widening of the diseased region becomes more pronounced.

Example 5

Multi-Link™ stents (available from Guidant Corporation) were cleaned by placement in an ultrasonic bath of isopropyl alcohol solution for 10 minutes. The stents were dried and plasma cleaned in a plasma chamber. An EVOH solution was made with 0.2 gram of Soarnol® D-2908 and 9.73 grams of IPA/H2O solvent, making an EVOH: IPA/H2O ratio of 1:49. Actinomycin-D was added to the solution. Actinomycin-D constituted 0.67% by weight of the total weight of the solution. The solution was vortexed and placed in a vial. The cleaned stents were attached to spray mandrels. The stents were passed under a spray head, for about 3 to 10 seconds, with rotational speed of 40 to 150 rpm and 0.5 mg per second atomized flow rate. The atomization pressure was kept at 15 psi. The coated stents were placed in a convection oven at 50° C. and cured for 5 to 20 minutes. The above process was repeated to have a minimal five layers. The final drying of the coated stents were performed in an oven at 50° C. for one to four hours. The average dried coating weight was 200 micrograms, with an estimated actinomycin D concentration of 50 micrograms per stent.

Example 6

Multi-Link™ stents were cleaned by placement in an ultrasonic bath of isopropyl alcohol solution for 10 minutes. The stents were dried and plasma cleaned in a plasma chamber. An EVOH solution was made with 0.2 gram of Soarnol D-2908 and 9.73 grams of IPA/H2O solvent, making an EVOH: IPA/H2O ratio of 1:49. Actinomycin-D was added to the solution. Actinomycin-D constituted 0.67% by weight of the total weight of the solution. The solution was vortexed and placed in a vial. The cleaned stents were attached to a spray mandrel. The stents were passed under a spray head, for about 3 to 10 seconds, with a rotation speed of 40 to 150 rpm and 0.15 mg per second atomized flow rate. The atomization pressure was kept at 10 psi. Interpass drying was applied by using the warm air (45° C.) flow. The above process was repeated to have a minimal ten layers. The final drying of the coated stents was in an oven at 50° C. for one to four hours. The average dried coating weight was 200 to 600 micrograms, with an estimated actinomycin D concentration of 50 to 140 micrograms per stent.

While particular embodiments of the present invention have been shown and described, it will be obvious to those skilled in the art that changes and modifications can be made without departing from this invention in its broader aspects and, therefore, the appended claims are to encompass within their scope all such changes and modifications as fall within the true spirit and scope of this invention.

What is claimed is:

1. A medical article, comprising:
    (a) an implantable medical device; and
    (b) a coating deposited on the medical device, the coating including an ethylene vinyl alcohol copolymer, wherein the copolymer can be dissolved when added to a solvent comprising iso-propyl alcohol and water.

2. The medical article of claim 1, wherein the copolymer comprises a mole percent of ethylene of about 27% to about 29%.

3. The medical article of claim 1, wherein the copolymer comprises a mole percent of ethylene of about 29%.

4. The medical article of claim 1, wherein the copolymer is SOARNOL.

5. The medical article of claim 1, wherein the prosthesis is selected from the group consisting of balloon-expandable stents, self-expandable stents, and grafts.

6. The medical article of claim 1, additionally comprising an active agent carried by the coating for inhibiting abnormal or inappropriate migration or proliferation of smooth muscle cells.

7. The medical article of claim 1, additionally comprising actinomycin D, or analogs or derivatives thereof, carried by the coating.

8. The medical article of claim 1, additionally comprising paclitaxel or docetaxel carried by the coating.

9. The medical article of claim 1, wherein the coating acts as an intermediary tie layer between a metallic surface of the prosthesis and a coating layer carrying an active agent.

10. The medical article of claim 1, wherein the coating acts a diffusion barrier disposed over a coating layer carrying an active agent for reducing the rate at which the active agent is released.

11. A therapeutic composition for inhibiting the narrowing of a region of a blood vessel, comprising an ethylene vinyl alcohol copolymer and an active agent,
wherein the copolymer comprises a mole percent of ethylene of about 27% to about 29%, and
wherein the active agent is released from the copolymer to inhibit the narrowing of a region of a blood vessel.

12. The therapeutic composition of claim 11, wherein the narrowing is caused by restenosis.

13. The therapeutic composition of claim 11, wherein the active agent is actinomycin D, paclitaxel, docetaxel, or analogs or derivatives thereof.

14. A solution for coating a medical device comprising:
(a) an amount of iso-propyl alcohol and water solvent;
(b) an amount of an ethylene vinyl alcohol copolymer dissolved in the solvent; and
(c) an amount of an active agent for inhibiting restenosis a blood vessel.

15. The solution of claim 14, wherein the active agent is actinomycin D, docetaxel, or paclitaxel.

* * * * *